United States Patent
Buelow et al.

(10) Patent No.: US 12,431,240 B2
(45) Date of Patent: Sep. 30, 2025

(54) INSTANT SCOUT SCAN CHECKER

(71) Applicant: KONINKLIJKE PHILIPS N.V., Eindhoven (NL)

(72) Inventors: Thomas Buelow, Grosshansdorf (DE); Hrishikesh Narayanrao Deshpande, Hamburg (DE); Tanja Nordhoff, Hamburg (DE); Tim Philipp Harder, Ahrensburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 443 days.

(21) Appl. No.: 18/017,100

(22) PCT Filed: Jul. 23, 2021

(86) PCT No.: PCT/EP2021/070706
§ 371 (c)(1),
(2) Date: Jan. 20, 2023

(87) PCT Pub. No.: WO2022/018270
PCT Pub. Date: Jan. 27, 2022

(65) Prior Publication Data
US 2023/0298745 A1  Sep. 21, 2023

Related U.S. Application Data

(60) Provisional application No. 63/055,918, filed on Jul. 24, 2020.

(51) Int. Cl.
G16H 40/63 (2018.01)
G06T 7/00 (2017.01)
(Continued)

(52) U.S. Cl.
CPC .......... *G16H 40/63* (2018.01); *G06T 7/0012* (2013.01); *G06T 7/10* (2017.01); *G16H 30/40* (2018.01); *G06T 2207/20081* (2013.01)

(58) Field of Classification Search
CPC .......... G16H 40/63; G16H 30/40; G06T 7/10; G06T 7/0012; G06T 2207/20081
See application file for complete search history.

(56) References Cited

U.S. PATENT DOCUMENTS 10,064,591 B2 * 9/2018 Wang ................... A61B 6/4441
2011/0246521 A1 10/2011 Luo
(Continued)

FOREIGN PATENT DOCUMENTS

EP  3447733 A1  2/2019
WO  2009/050676 A1  4/2009

OTHER PUBLICATIONS

International Search Report and Written Opinion Dated Nov. 24, 2021 for International Application No. PCT/EP2021/070706 Filed Jul. 23, 2021.

*Primary Examiner* — Quang N Vo
(74) *Attorney, Agent, or Firm* — Larry Liberchuk

(57) ABSTRACT

An apparatus (1) for use in conjunction with a medical imaging device (2) having an imaging device controller (4) that displays a graphical user interface (GUI) (8) including a preview image viewport (9). The apparatus includes at least one electronic processor (20) programmed to: receive a video feed (17) of the GUI displayed on the imaging device controller; extract a preview image (12) displayed in the preview image viewport from the live video feed of the GUI; perform an image analysis (38) on the extracted preview image to detect one or more image features (42) indicative of one or more potential problems associated with a medical imaging examination performed with the medical imaging device; and output an alert (30) when one or more
(Continued)

potential problems associated with the medical imaging examination is detected from the one or more image features.

20 Claims, 4 Drawing Sheets

(51) Int. Cl.
*G06T 7/10* (2017.01)
*G16H 30/40* (2018.01)

(56) References Cited

U.S. PATENT DOCUMENTS

| | | |
|---|---|---|
| 2014/0098932 A1 | 4/2014 | Profio |
| 2014/0270053 A1 | 9/2014 | Larson |
| 2015/0033073 A1 | 1/2015 | Yang |
| 2016/0037057 A1* | 2/2016 | Westin .................... G06F 16/51 348/207.1 |
| 2016/0062956 A1 | 3/2016 | Gotman |
| 2017/0069081 A1 | 3/2017 | Gluncic |
| 2017/0143284 A1 | 5/2017 | Sehnert |
| 2017/0265836 A1 | 9/2017 | Laor |

* cited by examiner

INSTANT SCOUT SCAN CHECKER

CROSS REFERENCE TO RELATED APPLICATIONS

This application is the U.S. National Phase application under 35 U.S.C. § 371 of International Application No. PCT/EP2021/070706 filed Jul. 23, 2021, which claims the benefit of U.S. Provisional Patent Application No. 63/055,918 filed Jul. 24, 2020. These applications are hereby incorporated by reference herein.

FIELD

The following relates generally to the imaging arts, imaging workflow setup arts, image quality assessment arts, real-time imaging acquisition feedback arts, and related arts.

BACKGROUND

With a trend to value-based care, quality management in medical imaging plays an increasingly important role. At the same time there is a shortage of well-trained staff (i.e., technologists). In computed tomography (CT), before the actual three-dimensional (3D) scan is performed, commonly a preview image in the form of a low-dose two-dimensional (2D) scout scan is conducted which is used, e.g., for planning of the field of view (FOV). Based on the scout scan, parameters such as the table height can be adjusted before the actual 3D scan is acquired. Preview images are also commonly acquired in the context of some other imaging modalities. For example, in magnetic resonance imaging (MRI) a fast, low resolution preview image may be acquired prior to plan the FOV prior to acquiring the 3D clinical images. In some instances, a shortage of staff can result in images being acquire with preventable quality issues, such as incorrect patient positioning, an incorrect FOV, foreign objects being present in the FOV, among others.

The following discloses certain improvements to overcome these problems and others.

SUMMARY

In one aspect, an apparatus for use in conjunction with a medical imaging device having an imaging device controller that displays a graphical user interface (GUI) including a preview image viewport. The apparatus includes at least one electronic processor programmed to: receive a video feed of the GUI displayed on the imaging device controller; extract a preview image displayed in the preview image viewport from the live video feed of the GUI; perform an image analysis on the extracted preview image to detect one or more image features indicative of one or more potential problems associated with a medical imaging examination performed with the medical imaging device; and output an alert when one or more potential problems associated with the medical imaging examination is detected from the one or more image features.

In another aspect, an apparatus for use in conjunction with a medical imaging device having an imaging device controller that displays a GUI including a preview image viewport. The apparatus includes at least one display device separate from the imaging device controller and a video cable splitter operatively connected with the imaging device controller. At least one electronic processor is programmed to: receive a video feed of the GUI displayed on the imaging device controller via the video cable splitter; extract a preview image displayed in the preview image viewport from the live video feed of the GUI; perform an image analysis on the extracted preview image to detect one or more image features indicative of one or more potential problems associated with a medical imaging examination performed with the medical imaging device; and output an alert when one or more potential problems associated with a medical imaging examination is detected from the one or more image features on the display device that is separate from the imaging device controller.

In another aspect, a method for providing real-time checking of one or more potential problems associated with a medical imaging examination includes: receiving a video feed of a GUI displayed on an imaging device controller; extracting a preview image displayed in a preview image viewport of the GUI from the live video feed; performing an image analysis on the extracted preview image to detect one or more image features indicative of one or more potential problems associated with a medical imaging examination performed with the medical imaging device; and output an alert when one or more potential problems associated with a medical imaging examination is detected from the one or more image features. The one or more potential problems include: a potentially obscuring object present in the preview image; a misplacement of a body part to be imaged of a patient in a field of view (FOV) of the preview image; a misplacement of a position of a table on which a patient to be imaged lies on during the medical imaging procedure based on an amount of the table visible in the preview image; and a disease condition of the patient based in the preview image.

One advantage resides in providing an automated approach for warning of the presence of foreign objects in a FOV prior to clinical images being acquired in an imaging examination.

Another advantage resides in providing an automated approach for warning of an incorrect FOV prior to clinical images being acquired in an imaging examination.

Another advantage resides in providing an automated approach for warning of an incorrect position of a patient in a FOV prior to clinical images being acquired in an imaging examination.

Another advantage resides in providing correct labels for images to be acquired in an imaging examination.

Another advantage resides in providing an automated approach for warning of a disease condition such as a tumor or bony growth automatically detected in a preview image acquired prior to clinical images being acquired in an imaging examination.

Another advantage resides in providing a FOV checking process for images to be acquired of a patient without modifying the imaging device controller to do so.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
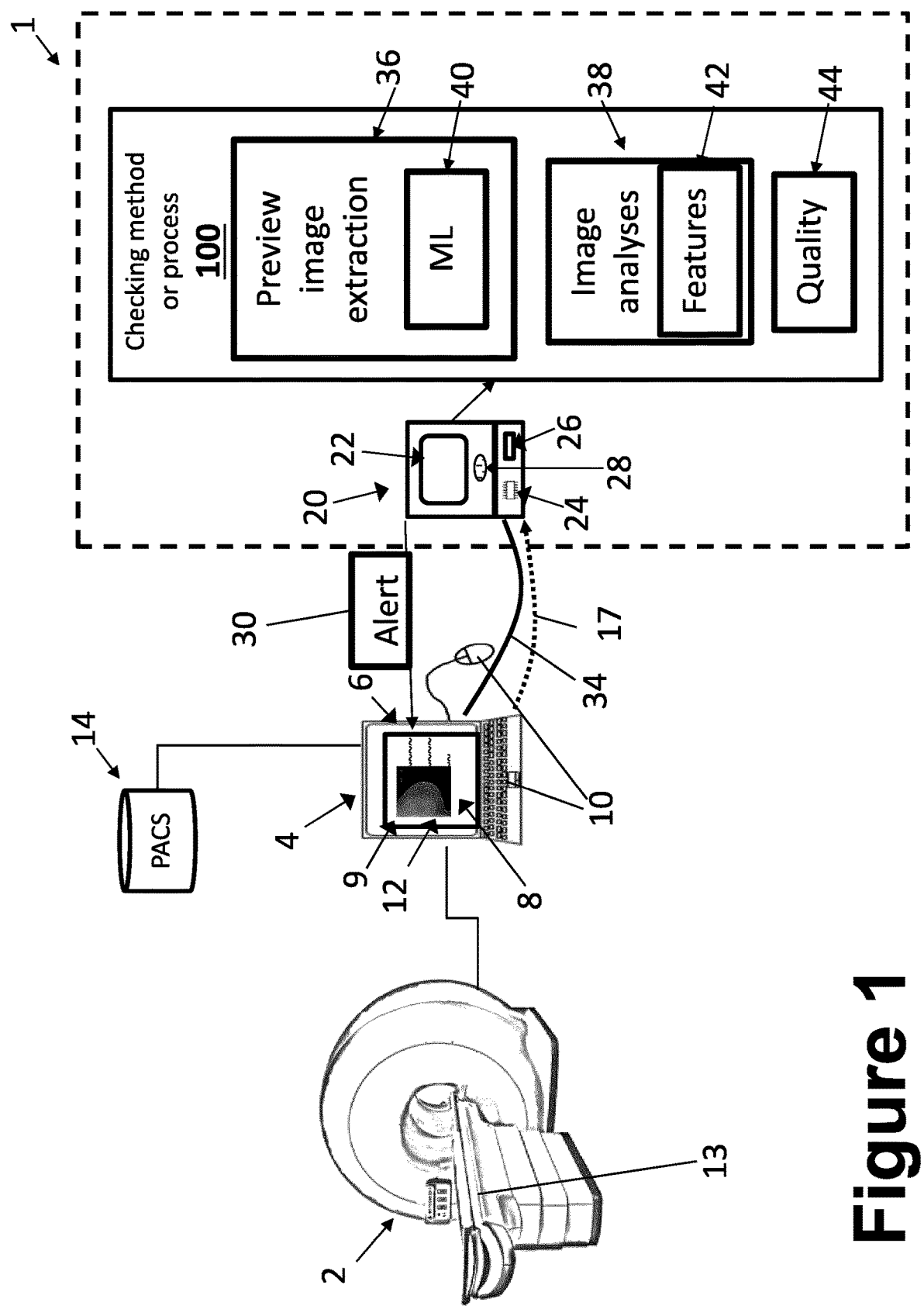
FIG. 1 diagrammatically illustrates an illustrative apparatus for checking a scout scan in accordance with the present disclosure.

The following discloses systems and methods for extracting the scout scan acquired by a CT scanner in order to check for issues before the clinical images are acquired. A scout scan is an example of a preview image, where a preview image is a "quick" scan that is usually a two-dimensional (2D) scan. Alternatively, the scout scan may be a low dose three-dimensional (3D) scan. In MRI, the scout scan be a low resolution (and hence fast) 2D or 3D scan. The scout scan is sometimes of a somewhat larger field of view (FOV) than the intended clinical images.

To provide vendor-agnostic operation, the illustrative system uses a DVI splitter, video camera, or the like to acquire a video feed of the CT scanner controller display, and to detect the scout scan (or other preview image) as a rectangular region with dark boundaries, e.g. using a machine learning (ML) tool or video frame image segmentation. For analyses requiring knowledge of the anatomy being imaged, the anatomy is suitably determined by analysis of the scout image, for example, automated image segmentation and comparison of the segmented regions with a reference image or atlas image. Alternatively, the knowledge of the anatomy being imaged can be obtained detecting a textual label in the captured video frame indicating the imaged anatomy.

Various checks are performed by analyzing the extracted scout scan. Jewelry or other potentially obscuring objects can be detected based on high Hounsfield unit (HU) values and/or segmentation. Misplacement of the patient in the FOV (not well centered and/or rotated, e.g. head tilt) can be detected using image segmentation and/or a trained ML tool. An error in table height can be detected in a lateral scout scan or in a frontal scout scan. In the latter case, the amount of table in the image can be used.

Another proposed analysis is to detect certain disease conditions, such as a tumor or bony growth, using segmentation or a ML tool.

The disclosed system can, in some embodiments, be implemented as a separate box connected via a DVI splitter, which includes a display for presenting notifications of any detected issues. The display in some embodiments is a text display presenting notification texts. Alternatively, in other embodiments the display is a (possibly low resolution) graphical display that shows the scout image (or, more generally, preview image, e.g. as extracted via the DVI splitter) with a superimposed arrow or other graphic highlighting the issue. For example, to indicate misplacement of the patient relative to the FOV, the superimposed indicator might be crosshairs indicating the vertical/horizontal centers of the FOV, and crosshairs indicating the vertical/horizontal center-of-mass of the anatomy being imaged. In other examples, the approach of analyzing a scout image to preemptively detect issues could also be performed in the scanner controller, in which case the DVI splitter would be omitted.

In computed tomography (CT), acquisition of a preview image in the form of a 2D scout image is common practice. However, preview images are also acquired in other imaging modalities such as Magnetic Resonance Imaging (MRI) in which a fast, low resolution and/or low dose and/or 2D preview image is acquired during imaging setup, and the disclosed approaches employing extraction and analysis of a preview image can be employed with such other modalities (e.g. MRI) as well.

With reference to FIG. 1, an illustrative apparatus 1 providing immediate scout scan (or, more generally, preview image) checking processes during an imaging examination is shown. The apparatus 1 is used in conjunction with an image acquisition device 2, which can be (by way of nonlimiting illustrative examples) a Magnetic Resonance (MR) image acquisition device, a Computed Tomography (CT) image acquisition device; or a medical imaging device of another modality. The imaging device 2 may also be a hybrid imaging device such as a PET/CT or SPECT/CT imaging system. The medical imaging device 2 is controlled via an imaging device controller 4, which includes a display 6 on which a graphical user interface (GUI) 8 is presented to a user (e.g., an imaging technician), and one or more user input devices 10 (e.g. keyboard, trackpad, mouse, et cetera) via which the user interacts sets up and controls the medical imaging device 2 to acquire clinical images. The apparatus 1 also includes a preview image viewport 9 displayed via the GUI 8.

In the process of setting up to acquire the clinical images, the GUI 8 is operated to cause the medical imaging device 2 to acquire and display a preview image 12 as the scout scan on the preview image viewport 9. The preview image 12 is usually acquired and displayed at a lower resolution than the clinical image(s) that are subsequently acquired, but is sufficient for the user to verify that the correct anatomy is being imaged, that the anatomy is correctly positioned, is of a usefully large size (but not too large) in the image, and so forth. When the user is satisfied, based on the preview image 12 and other information, that the imaging device 2 is correctly set up to acquire the desired clinical image(s), the user operates the GUI 8 to initiate the clinical imaging, reviews the acquired clinical images on the display 6, and ultimately stores the final clinical images to a Picture Archiving and Communication System (PACS) database 14, along with image labels created from image label information generated by the GUI navigation and/or data entry (or, in some cases, auto populated into the GUI dialogs from the RIS or other linked database).

While the imaging technician is expected to use the preview image to check for various possible issues before acquiring the clinical images, there is a possibility that the technician may fail to notice a problem shown in the preview image. For example, the technician may fail to notice incorrect patient positioning, or presence of a metal artifact in the patient, or so forth. Such an error is made more likely by the workload imposed on many imaging technicians, who are expected to complete an imaging examination in a predefined time interval. Failure to detect problems at the preview image stage can lead to the need to re-acquire subsequent clinical images during the current imaging examination (if the problem is noticed in the clinical images prior to storing to the PACS) or to the need for a complete repeat of the imaging examination (if the problem is only noticed when a radiologist downloads the clinical images from the PACS for review). Hence, failure to detect a problem at the preview image stage is costly for the radiology department and can inconvenience the patient and/or increase the dose load to the patient.

To address such problems, FIG. 1 also discloses the apparatus 1 for providing immediate automated analysis of a preview image at the time of its acquisition and display. The apparatus 1 is preferably, although not necessarily, a separate device from the imaging device controller 4. For example, the apparatus 1 may comprise a computer or other electronic processing device 20 embodied as a notebook computer, tablet computer, a Raspberry Pi or other single-board computer, or so forth) and includes a display 22, an electronic processor (e.g. one or more microprocessors) 24 and a non-transitory storage medium 26. (Note, the electronic processor 24 and a non-transitory storage medium 26 are diagrammatically shown in FIG. 1, but are typically internal components, e.g. housed inside the housing of the computer 20). The display 22 presents one or more alerts 30 when a potential problem associated with the medical imaging examination is detected in the preview image 12. Optionally, the apparatus 1 further includes a loudspeaker 28, e.g. mounted in or on the computer 20, for providing an audible indication when an alert 30 is presented.

While the apparatus 1 typically employs a standalone computer 20 or the like as the data processing device, it is contemplated for some data processing involved in providing the immediate preview image checking (for example, computationally complex image analyses) to be implemented on a remote server (not shown) that is connected with the local electronic processing device 20 via a wired or wireless data communication connection. For example, the remote server may be a hospital server, cloud computing resource, or so forth connected with the local computer 20 via a hospital electronic network and/or the Internet. The display device 22 can be of any size, but to provide the apparatus 1 as a compact unit that can be conveniently positioned next to (or otherwise near to) the imaging device controller 4, the display 22 is typically relatively small, e.g. a 5-inch display, 10-inch display, 12-inch display, or so forth. In some embodiments, the apparatus 20 does not have any user input devices (i.e., nothing analogous to the keyboard, mouse, or other user input device 10 of the imaging device controller 4), although it is alternatively contemplated for the computer or other electronic processing device 20 to include a keyboard or the like for setting up the preview image checking software or for other purposes. The non-transitory storage medium 26 may, by way of non-limiting illustrative example, comprise one or more of a hard disk or other magnetic storage medium, a solid state drive (SSD), flash memory, or other electronic storage medium, an optical disk or other optical storage medium, various combinations thereof, and/or so forth.

In one example embodiment, both the apparatus 1 and the imaging device controller 4 can be operated by a single technologist in a single room. In another embodiment, both the apparatus 1 and the imaging device controller 4 can be operated by a single technologist in separate rooms. In another example, the apparatus 1 can be disposed in a remote location from the imaging device controller 4 and be operated by a single technologist, who can provide assistance to another technologist in the room housing the imaging device controller.

The electronic processing device 20 of the illustrative checking apparatus 1 is operatively connected to receive a live video feed 17 of the display 6 of the imaging device controller 4. The live video feed 17 is, in the illustrative embodiment, provided by a video cable splitter 34 (e.g., a DVI splitter, a HDMI splitter, and so forth). In other embodiments, the live video feed 17 may be provided by a video cable connecting an auxiliary video output (e.g. aux vid out) port of the imaging device controller 4 to the electronic processing device 20 of the immediate scout scan checker apparatus 1. This latter approach may be useful, for example, if the imaging device 2 is a compact ultrasound imaging device with an integral display, in which case it may not be convenient to connect a video cable splitter since the wiring of the display is in this case the wiring to the ultrasound display is entirely internal to the ultrasound imaging device cabinet—but, an "aux vid out" port may be provided in such a portable ultrasound imaging device. In another contemplated embodiment, screen-sharing software running on the imaging device controller 4 and the electronic processing device 20 provides the live video feed 17 to the electronic processing device 20. These are merely illustrative examples. Moreover, in alternative embodiments in which the checker is implemented in the imaging device controller 4, there is no need for the live video feed extraction as the preview image 12 is directly available to the imaging device controller 4.

The final clinical images are saved to the PACS 14 with image label information labeled thereto, typically in the form of DICOM labels or tags. As used herein, the term "image label information" (and variants thereof) refers to information extracted from the live video feed 17 of the imaging device controller 4 indicating a DICOM label of the clinical image (which may or may not yet be acquired). The image label information does not label the preview image 12, as the preview image is not saved to the PACS 14. In addition, the image label information does not constitute actual DICOM labels or tags with which the clinical image is (or will be) labeled.

The non-transitory storage medium 26 of the apparatus 1 stores instructions which are readable and executable by the at least one electronic processor 24 of the apparatus 1 (which as previously noted, is contemplated to include a remote server or servers on a local area network or the Internet) to perform disclosed operations including performing a method or process 100 for providing immediate checking of the preview image at the time it is displayed on the imaging device controller 4 during an imaging examination. The checking method or process 100 includes a preview image extractor method or (sub-)process 36, and one or more image analyses 38, In some embodiments, the at least one electronic processor 20 of the workstation 12 is programmed to implement at least one machine-learning ML component 40 (e.g., one or more convolutional neural networks (CNNs)) to extract the preview image 12 from the tapped live video feed 17. In some examples, the method 100 may be performed at least in part by cloud processing.

Figure 2:
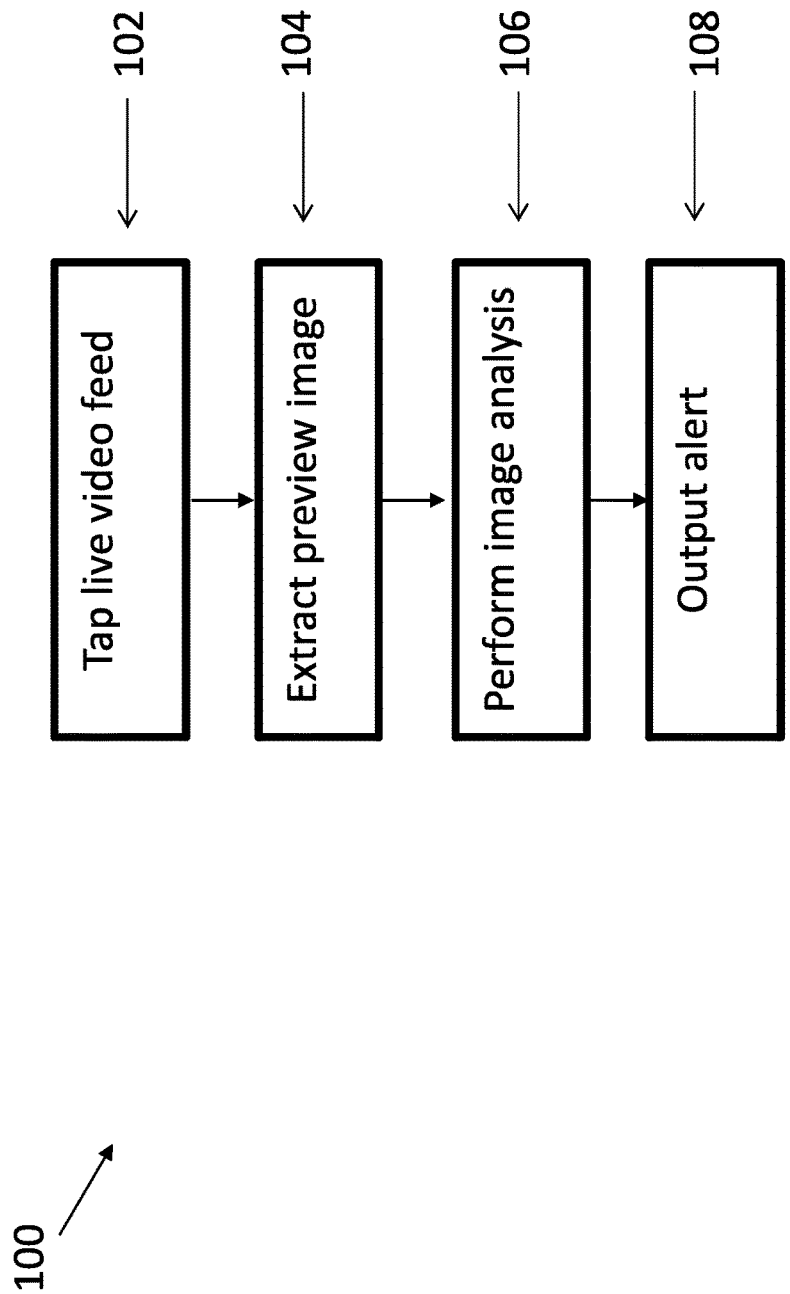
FIG. 2 shows example flowchart operations performed by the apparatus of FIG. 1.

With reference to FIG. 2, and with continuing reference to FIG. 1, an illustrative embodiment of the method 100 is diagrammatically shown as a flowchart. The method 100 is performed prior to a medical imaging examination performed using the medical imaging device 2. At an operation 102, the electronic processing device 20 is programmed to receive the live video feed 17 of the imaging device controller 10 of the medical imaging device 2, e.g. via the video cable splitter 34.

At an operation 104, the electronic processing device 20 is programmed to extract the preview image 12 from the received live video feed 17. The extracted preview image 12 is displayed in the preview image viewport 9. To do so, the at least one electronic processor 20 in some embodiments is programmed to determine at least one of a modality of the imaging device 2 and/or an anatomy of a patient being imaged by the imaging device. For example, an OCR process can be performed on the live video feed 17 to relevant text identifying the modality and/or the anatomy. In another example, an image matching process can be performed on the live video feed 17 to graphical elements identifying the modality and/or the anatomy.

Based on the determined modality or imaged anatomy part, and/or attributes of the preview image displayed in the viewport (such as, for example, an identified rectangular border region), video frames from the tapped live video feed 17 are analyzed to detect the video frame containing the preview image 12. In some examples, the preview image 12 can be identified as a region having a boundary (e.g., a rectangular boundary) that is darker than a remainder of the received video feed 17. To do so, the at least one trained ML component (e.g., CNN) 40 is applied to the tapped live video feed 17 to detect and extract the preview image 12. In one example, the CNN 40 is configured to detect the preview image 12 by identifying, in the tapped live video feed 17, at least one of: a rectangular gray scale region with a dark boundary, size characteristics of a preview image, and location characteristics of a preview image.

At an operation 106, the electronic processing device 20 is programmed to perform an image analysis 38 on the extracted preview image 12 to detect or extract one or more image features 44 indicative of one or more potential problems associated with a medical imaging examination performed with the medical imaging device. To do so, in one example, the at least one trained ML component 40 is applied to the extracted preview image 12 to detect the image features 44. (In alternative embodiments implemented in the imaging device controller 4, the operation 106 suitably operates on the preview image 12 which is directly available at the imaging device controller 4, in which case the operations 102, 104 are suitably omitted.) In another example, the image features 44 can be identified by an image segmentation process.

The operation 106 can be performed in a variety of manners. In one example, the electronic processing device 20 is programmed to perform the image analysis 38 on the extracted features 44 to identify misplacement of a body part imaged in a FOV by the extracted preview image 12. The misplacement can be due to an improper positioning or orientation of the patient based on how much of the patient is visible in the preview image 12. In another example, the displacement can be due to misplacement of the patient on a table 13 of the medical imaging device 2. This can be detected based on how much of the table 13 is present in the preview image 12. In another example, the electronic processing device 20 is programmed to perform the image analysis 38 to identify on the extracted features 44 a potentially obscuring object present in the preview image (e.g., based on, for example, high Hounsfield Unit (HU) values, or detecting foreign objects by ML algorithms, and so forth). The potentially obscuring object can be, for example, jewelry, metal parts in clothing, and so forth). In another example, the electronic processing device 20 is programmed to perform the image analysis 38 to identify on the extracted features 44 a disease condition of the patient. These are merely non-limiting examples.

The use of the video feed 17 as the information source in the illustrative embodiment advantageously enables the apparatus 1 to be used in conjunction with numerous different modalities/imaged anatomies, and without modifying the imaging device controller 4. Moreover, what the apparatus 1 detects is potential problems associated with the medical imaging examination performed with the medical imaging device. Given an alert indicating such an inconsistency, the imaging technician can then review the situation to determine whether it is the preview image 12 that is incorrect, or whether one or more potential problems associated with the medical imaging examination is detected.

In an alternative approach, if the apparatus 1 is designed to work with only a specific imaging modality then there is no need to determine the modality, and this aspect of operations 104-106 can be omitted. Likewise, if the apparatus 1 is designed to work with only a specific imaged anatomy (e.g., in the case of a dedicated mammography imaging system, the anatomy is a breast) then there is no need to determine the imaged anatomy, and this aspect of operations 104-106 can be omitted.

In some embodiments, the potential findings can be logged for training purposes. For example, the potential problems can be input to an outcomes-based quality module 44 for processing (i.e., comparing the input potential problems to ground truth values). The outcomes-based quality module 44 can check whether the one or more potential problems are valid. In this way, it can be determined if individual technicians (or groups of technicians) have issues spotting certain potential problems that might result in error and/or if certain recommendations were not corrected that resulted in issues in the final image saved to the PACS 14. This data can be used in creating or selecting educational content for the remote experts RE and/or the local operators LO.

In other embodiments, the outcomes-based quality metric module 44 is programmed to take the results of whether the one or more potential problems are valid, and used to suggest improvements in the imaging workflow. These improvements can be used for hospital effectiveness, with potential ties to reimbursement.

At an operation 108, the electronic processing device 20 is programmed to output the alert 30 when one or more potential problems associated with the medical imaging examination is detected from the one or more image features 44. The alert 30 can indicate, for example, the presence of a potentially obscuring object in the preview image 12, an identification of the misplacement of the body part to be imaged present in the preview image, an identification of the misplacement of the position of the table 13, an identification of the disease condition of the patient, and so forth.

The alert 30 can be any suitable alert, including, for example, a textual alert on the display device 6 of the imaging device controller 4 or the display device 22 of the apparatus 1, an audible alarm via the loudspeaker 28, graphical annotations on the extracted preview image displayed on the display 22, and so forth. In one example, the preview image 12 can be displayed with superimposed graphical annotations (comprising the alert 30) can be displayed on the display device 22. In another example, at least one frame of the video feed 17 of the GUI 8 can be displayed with superimposed annotations (comprising the alert 30) identifying the inconsistency of, for example, label information of the image.

Figure 3:
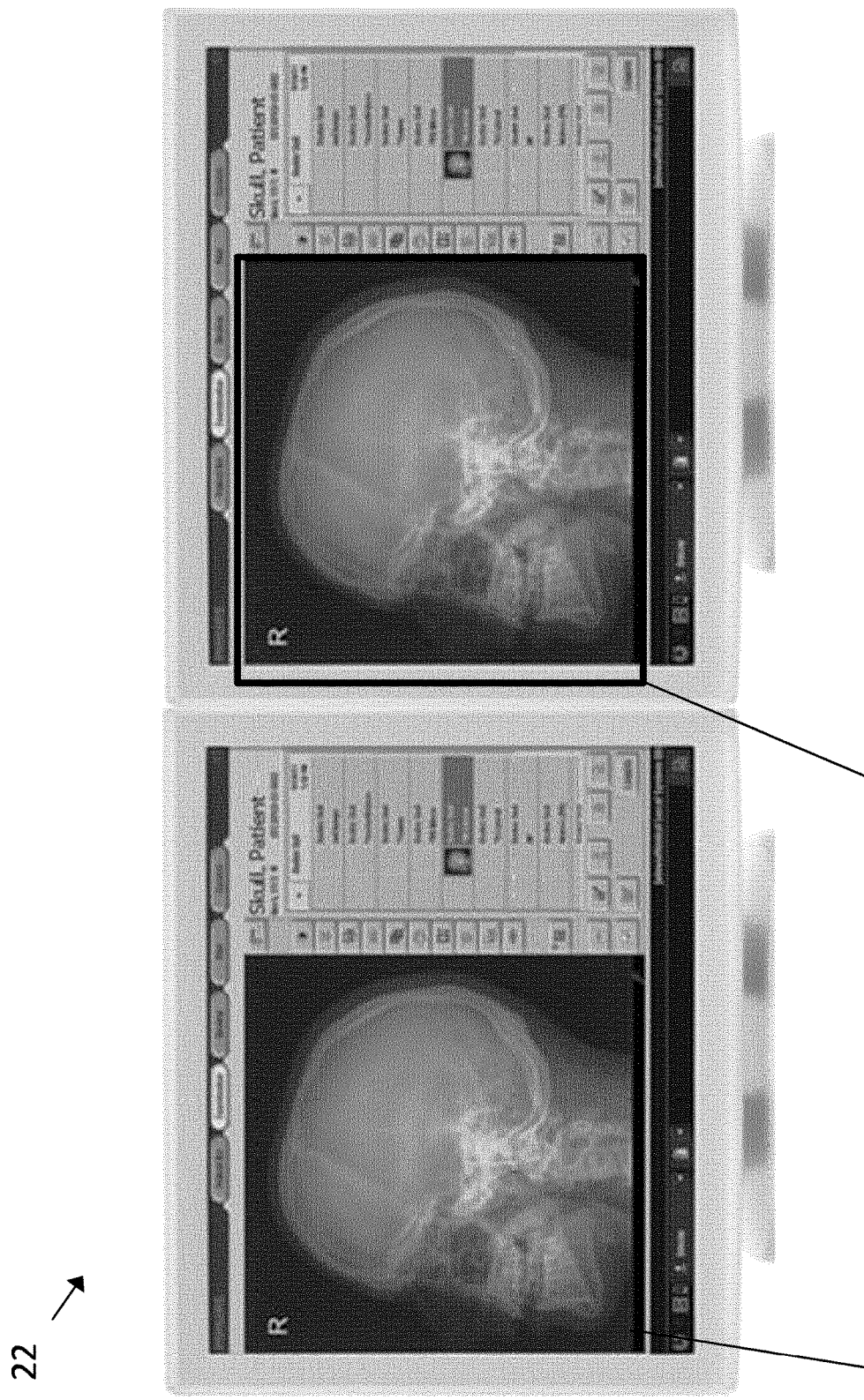
FIG. 3 shows an example of alerts displayed on the apparatus of FIG. 1.

FIG. 3 shows an example of the preview image 12 as shown on the display device 22 (or the display 6). As shown in FIG. 3, the preview image 12 is shown as a dark rectangular boundary relative to the rest of the received video feed 17. In addition, the alert 30 can also be shown on the display device 22 (or the display 6). The alert 30 can be textual messages (e.g., "remove jewelry" when the preview image 12 includes jewelry) In addition, the alert 30 can include advice for the technologist to resolve the issues (e.g., "consider re-position the patient" or "consider moving the table").

Figure 4:
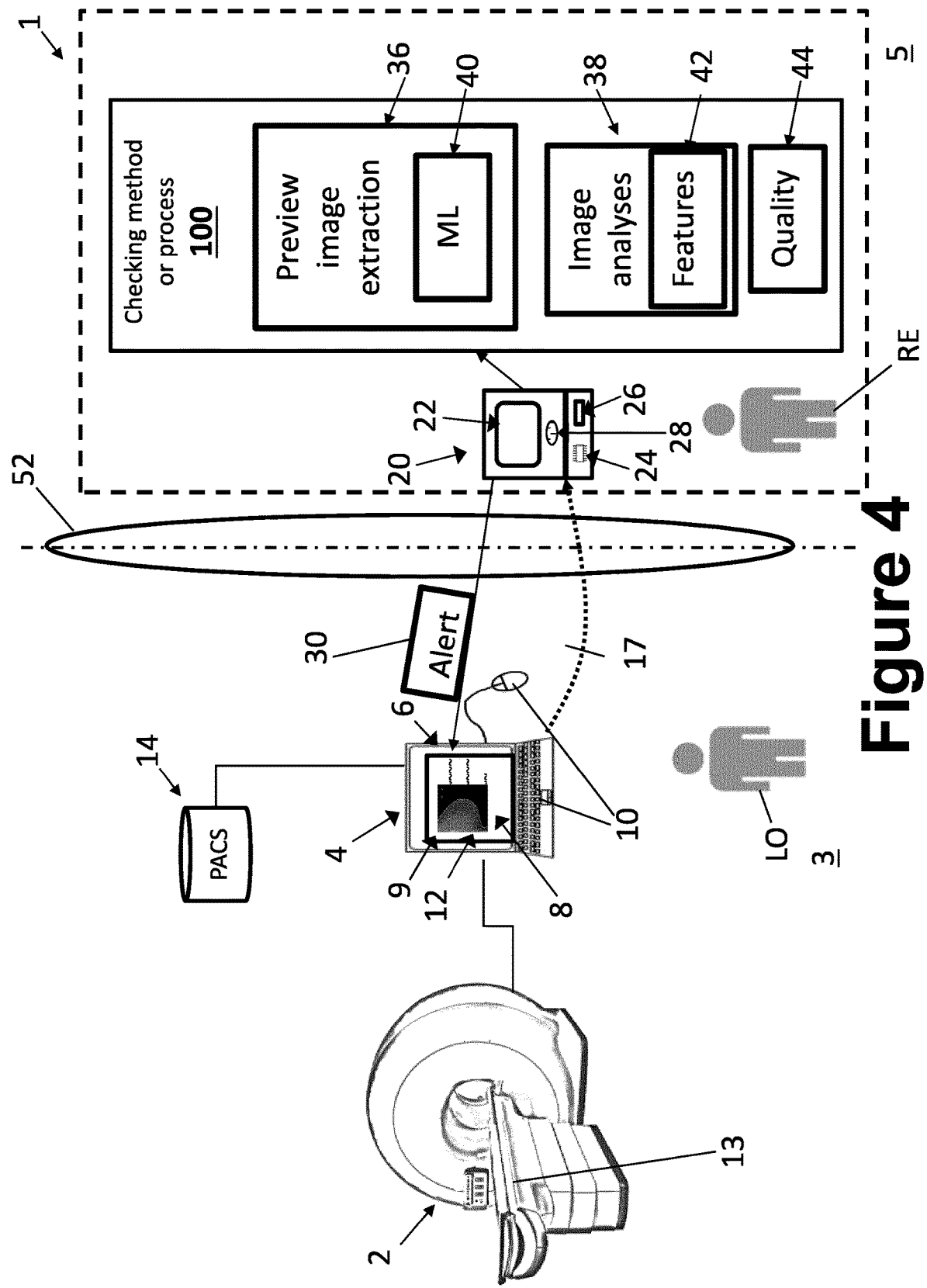
FIG. 4 diagrammatically another embodiment of the illustrative apparatus of FIG. 1.

As noted, the apparatus 1 can be disposed in a remote location from the imaging device controller 4 and be operated by a single technologist, who can provide assistance to another technologist in a room housing the imaging device controller. FIG. 4 shows an example of such a setup. As shown in FIG. 4, a local operator LO, who operates the medical imaging device 2, is located in a medical imaging device bay 3, and a remote expert RE is disposed in a remote service location or center 5 (e.g., a Remote Operations Command Center (ROCC)). The workspace of the imaging technicians may include other associated areas, such as a waiting room at each site (e.g., each radiology laboratory) where patients who have arrived for an imaging examination wait to be led into an imaging bay for the examination. It should be noted that the "remote expert" RE may not necessarily directly operate the medical imaging device 2, but rather provides assistance to the local operator LO in the form of advice, guidance, instructions, or the like via the alert 30. The remote location 5 can be a remote service center, a radiologist's office, a radiology department, and so forth. The remote location 5 may be in the same building as the medical imaging device bay 3 (this may, for example, in the case of a "remote operator or expert" RE who is a radiologist tasked with peri-examination image review), but more typically the remote service center 5 and the medical imaging device bay 3 are in different buildings, and indeed may be located in different cities, different countries, and/or different continents. In general, the remote location 5 is remote from the imaging device bay 3 in the sense that the remote expert RE cannot directly visually observe the imaging device 2 in the imaging device bay 3 (hence optionally providing the video feed 17).

As shown in FIG. 4, the video cable splitter 34 is omitted, and the imaging device controller 4 and the apparatus 1 are connected electronically (e.g., via a wireless network 52 such as the Internet) so that the imaging device controller 4 and the apparatus 1 can transmit the video feed 17 and the alert 30, respectively, to each other.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for use in conjunction with a medical imaging device having an imaging device controller that displays a graphical user interface (GUI) including a preview image viewport, the apparatus comprising at least one electronic processor programmed to:
receive a video feed of the GUI displayed on the imaging device controller;
extract a preview image displayed in the preview image viewport from the live video feed of the GUI;
perform an image analysis on the extracted preview image to detect one or more image features indicative of one or more potential problems associated with a medical imaging examination performed with the medical imaging device; and
output an alert when one or more potential problems associated with the medical imaging examination is detected from the one or more image features.

2. The apparatus of claim 1, wherein the image analysis includes:
applying at least one trained machine-learning (ML) component to the extracted preview image to detect the one or more image features.

3. The apparatus of claim 1, wherein the image analysis to identify the one or more image features is performed by an image segmentation process.

4. The apparatus of claim 1, wherein the image analysis is operative to identify, from the one or more image features, a potentially obscuring object present in the preview image based on high Hounsfield Unit (HU) values; and
the alert is indicative of an identification of the potentially obscuring object present in the preview image.

5. The apparatus of claim 1, wherein the image analysis is operative to identify, from the one or more image features, a misplacement of a body part to be imaged of a patient in a field of view (FOV) of the preview image; and
the alert is indicative of an identification of the misplacement of the body part to be imaged present in the preview image.

6. The apparatus of claim 1, wherein the image analysis is operative to identify, from the one or more image features, a misplacement of a position of a table on which a patient to be imaged lies on during the medical imaging procedure based on an amount of the table visible in the preview image; and
the alert is indicative of an identification of the misplacement of the position of the table.

7. The apparatus of claim 1, wherein the image analysis is operative to identify, from the one or more image features, a disease condition of the patient based in the preview image; and
the alert is indicative of an identification of the disease condition of the patient.

8. The apparatus of claim 1, wherein the at least one electronic processor is programmed to extract the preview image by:
identifying the preview image as a region having a boundary darker than a remainder of the received video feed.

9. The apparatus of claim 1, wherein the at least one electronic processor is programmed to extract the preview image by:
performing optical character recognition (OCR) on the live video feed of the GUI to generate OCR text; and
determining at least a portion of the preview image based on the OCR text.

10. The apparatus of claim 1, further including:
at least one display device separate from the imaging device controller,
wherein the at least one electronic processor is programmed to output the alert on the display device that is separate from the imaging device controller.

11. The apparatus of claim 10, wherein the at least one electronic processor is programmed to output the alert by:
displaying, on at least one display device that is separate from the imaging device controller, the preview image with superimposed graphical annotations.

12. The apparatus of claim 9, wherein the at least one electronic processor is programmed to output the alert by:
displaying, on at least one display device that is separate from the imaging device controller, at least one frame of the video feed of the GUI with superimposed annotations identifying the one or more potential problems associated with the medical imaging examination.

13. The apparatus of claim 1, wherein the at least one electronic processor is programmed to:
   input the detected one or more potential problems to an outcomes-based quality check module; and
   determine whether the detected one or more potential problems are valid.

14. The apparatus of claim 13, wherein the at least one electronic processor is programmed to:
   provide indications of improvements to a workflow based on whether the detected one or more potential problems are valid.

15. The apparatus of claim 1, wherein the medical imaging device and the imaging device controller are disposed in a medical imaging device bay, and the at least one electronic processor is disposed in a remote location from the medical imaging device.

16. An apparatus for use in conjunction with a medical imaging device having an imaging device controller that displays a graphical user interface (GUI) including a preview image viewport, the apparatus comprising:
   at least one display device separate from the imaging device controller;
   a video cable splitter operatively connected with the imaging device controller; and
   at least one electronic processor programmed to:
      receive a video feed of the GUI displayed on the imaging device controller via the video cable splitter;
      extract a preview image displayed in the preview image viewport from the live video feed of the GUI;
      perform an image analysis on the extracted preview image to detect one or more image features indicative of one or more potential problems associated with a medical imaging examination performed with the medical imaging device; and
      output an alert when one or more potential problems associated with a medical imaging examination is detected from the one or more image features on the display device that is separate from the imaging device controller.

17. The apparatus of claim 16, wherein the image analysis includes:
   applying at least one trained machine-learning (ML) component to the extracted preview image to detect the one or more image features.

18. The apparatus of claim 16, wherein the at least one electronic processor is programmed to output the alert by:
   displaying, on at least one display device that is separate from the imaging device controller, the preview image with superimposed graphical annotations.

19. The apparatus of claim 16, wherein the at least one electronic processor is programmed to output the alert by:
   displaying, on at least one display device that is separate from the imaging device controller, at least one frame of the video feed of the GUI with superimposed annotations identifying the one or more potential problems associated with the medical imaging examination.

20. A method for providing real-time checking of one or more potential problems associated with a medical imaging examination, the method including:
   receiving a video feed of a graphical user interface (GUI) displayed on an imaging device controller;
   extracting a preview image displayed in a preview image viewport of the GUI from the live video feed;
   performing an image analysis on the extracted preview image to detect one or more image features indicative of one or more potential problems associated with a medical imaging examination performed with the medical imaging device; and
   output an alert when one or more potential problems associated with a medical imaging examination is detected from the one or more image features;
   wherein the one or more potential problems include: a potentially obscuring object present in the preview image; a misplacement of a body part to be imaged of a patient in a field of view (FOV) of the preview image; a misplacement of a position of a table on which a patient to be imaged lies on during the medical imaging procedure based on an amount of the table visible in the preview image; and a disease condition of the patient based in the preview image.

* * * * *